United States Patent [19]

Anthony

[11] Patent Number: 4,681,544
[45] Date of Patent: * Jul. 21, 1987

[54] ORAL PACK RETENTION SYSTEM

[76] Inventor: Albert J. Anthony, 45 Central St., West Boylston, Mass. 01583

[*] Notice: The portion of the term of this patent subsequent to Aug. 6, 2002 has been disclaimed.

[21] Appl. No.: 762,932

[22] Filed: Aug. 6, 1985

Related U.S. Application Data

[63] Continuation-in-part of Ser. No. 457,762, Jan. 13, 1983, Pat. No. 4,533,326, Ser. No. 458,298, Jan. 17, 1983, Pat. No. 4,464,114, and Ser. No. 291,445, Aug. 10, 1981, abandoned.

[51] Int. Cl.⁴ ............................................. A61C 5/00
[52] U.S. Cl. ..................................... 433/215; 433/229
[58] Field of Search ................ 433/215, 229; 604/897

[56] References Cited

U.S. PATENT DOCUMENTS

4,286,592  1/1981  Chandrasekaran ................ 604/897

Primary Examiner—Robert Peshock
Attorney, Agent, or Firm—Blodgett & Blodgett

[57] ABSTRACT

A system for protecting oral tissue or retaining an object at a location in the mouth, consisting of a body of polymeric material extending from a tooth and over the tissue or location and a retaining means which attaches the material to the tooth. The object might be a medication delivery device, and, in particular, a medicated strip which can be inserted into a periodontal pocket. The retaining means might be a fixture tied to or adhesively bonded to the tooth, or the material might be directly adhesively bonded to the tooth. The polymeric material would be specially formulated to suit this application.

11 Claims, 13 Drawing Figures

ORAL PACK RETENTION SYSTEM

This is a continuation-in-part of copending application Ser. No. 457,762 filed on Jan. 13, 1983 and now U.S. Pat. No. 4,533,326 issued 8/06/85 and continuation-in-part of 458,298 filed 1/17/83 now and U.S. Pat. No. 4,464,114, issued 8/07/84 and continuation-in-part of 291,445 filed 8/10/81 now abandoned.

BACKGROUND OF THE INVENTION

After a dentist has performed one of a variety of types of surgery in the mouth of a patient, it is necessary to protect the surgical site. For that purpose, it is common practice to use a so-called "pack" in the form of an elastomer plastic. Unfortunately, for one reason or another, it is difficult to maintain the pack in place and they tend to become loosened, lost prematurely, and sometimes even swallowed. If this occurs, the surgerized tissue is not protected and the resulting trauma may cause pain, hemorrhage, or susceptibility to infection. A particularly important use for the pack is in the case of the free gingival graft where it is difficult to retain the pack on the donor site on the palate. In that case, it is particularly important to protect the site from which the tissue surface has been removed. Prior to the present invention, the only method of pack retention with any efficiency at all was the "surgical stent" which is a custom-made appliance. These appliances are very time consuming and expensive to make and are relatively uncomfortable for the patient. For these reasons, they are not usually constructed unless very extensive donor sites require dressing (surgical pack). The stent can easily be too lose or too tight, resulting in the loss of the pack. The stent also often allows liquids to seep to the raw tissue causing severe pain. Attempts have been made in the past to provide a means of holding the pack in place, but they have been less than successful, particularly when the wound was located in the palate. These and other difficulties experienced with the prior art devices have been obviated in a novel manner by the present invention.

It is, therefore, an outstanding object of the invention to provide an oral pack retention device to maintain a surgical pack securely in place.

Another object of this invention is the provision of an appliance for periodontal or oral surgical use, where the wound is located on the palate.

Still another object of this invention is the provision of an oral pack system adapted to hold a non-sticking dressing over a wound within the mouth.

An additional object of this invention is the provision of an oral pack system adapted to hold medication in a cavity in the mouth.

A further object of the present invention is the provision of a surgical pack retention device that is adaptable to all positions in the mouth irrespective of the shape, nature, or location of the tooth.

It is another object of the instant invention to provide a periodontal appliance which is simple and rugged in construction, which can be readily manufactured from easily obtainable materials, and which is capable of being sterilized either by autoclave or high dry heat.

It is another object of the instant invention to provide a periodontal appliance which is inexpensive to manufacture and which can be easily applied to either large or small surgical sites.

With these and other objects in view, as will be apparent to those skilled in the art, the invention resides in the combination of parts set forth in the specification and covered by the claims appended hereto.

SUMMARY OF THE INVENTION

In general, the invention consists of a oral pack retention system for use in maintaining a pack in place and having a retention fixture adapted to be located adjacent a tooth. A flexible wire is provided which extend around the tooth and is fastened to the fixture.

Specifically, the fixture has an extruded shape and both the fixture and the wire are formed of stainless steel.

BRIEF DESCRIPTION OF THE DRAWINGS

The character of the invention, however, may be best understood by reference to its structural forms, as illustrated by the accompanying drawings, in which.

DESCRIPTION OF THE PREFERRED EMBODIMENT

Figure 1:
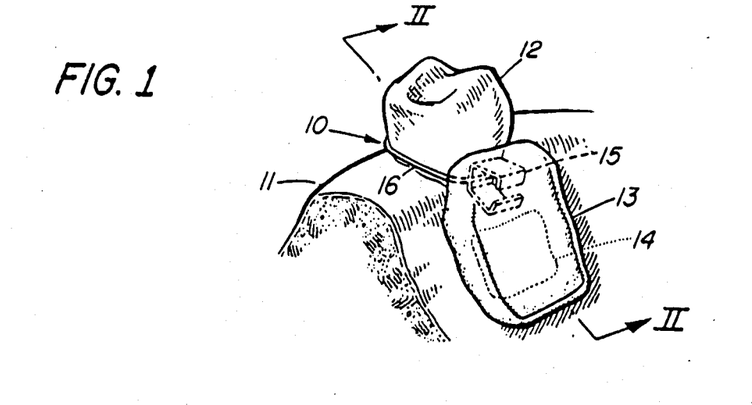
FIG. 1 is a perspective view of a oral pack retention device incorporating the principles of the present invention.

Referring first to FIG. 1, wherein are best shown the general features of one embodiment of the invention, the oral pack retention device, indicate generally by the reference numeral 10, is shown in use in a patient's mouth, having a palatal tissue surface 11 and a tooth 12. The device is shown in use holding a surgical pack 13 over a surgical donor site 14 on the palate 11.

Figure 2:
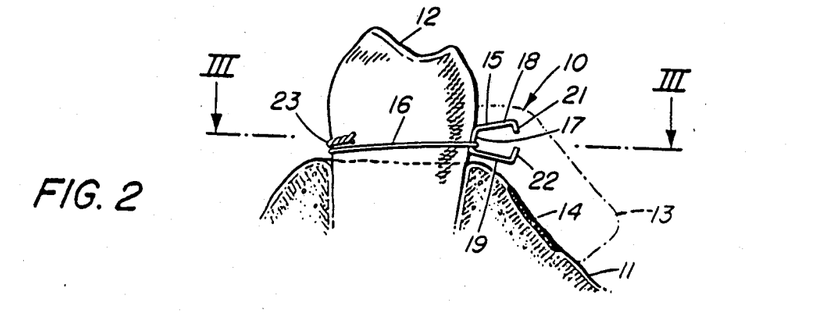
FIG. 2 is a vertical sectional view of the device taken on the line II—II of FIG. 1.
Figure 3:
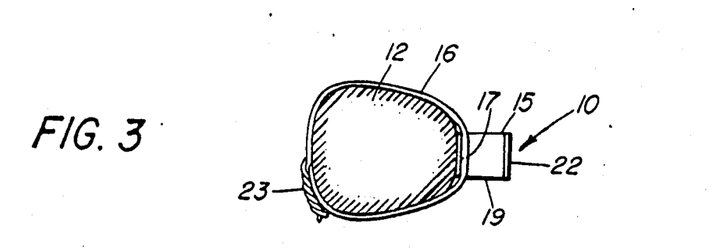
FIG. 3 is a plan view of the device as viewed on the line III—III of FIG. 2.

FIGS. 2 and 3 show the details of the oral pack retention device 10 which has a retention device 15 located adjacent the tooth 12. The device is provided with a wire 16 which extends tightly around the tooth and is fastened to the fixture 15. As is evident in FIG. 2, the fixture 15 has an extruded shape, that is to say, it has a constant cross-section. The wire 16 and the fixture 15 are formed of a non-corrosive material such as stainless steel. The fixture 15 has a flat central portion 17 which lies against the tooth and which is fastened to the wire 16 by welding or the like. The fixture 15 is also provided with arms 18 and 19 which extend laterally away from the central portion 17 at the top and bottom, respectively. These arms extend at an obtuse angle to the central portion. The outer end of the upper arm 18 is provided with a downwardly-extending flange 21, while a similar flange 22 extends upwardly from the outer end of the lower arm 19. The flanges, therefore, extend toward one another to the extent that they each occupy approximately one-third of the space between the ends of the arms.

The method of operation and the advantages of the present invention will now be readily understood in view of the above description. When the surgery (especially a free gingival graft) has been completed, the result is a raw connective tissue area without the normal epithelial covering at the site 14. When the surgery has been completed, it is necessary to apply the pack 13 to protect it and assist in healing. For that purpose, the fixture 15 with the wire 16 attached, is placed against the inner surface of the tooth 12 at a location which is close to where the tooth emerges from the gingiva 11. The ends of the wire 16 are carried around to the outer side of the tooth where they are twisted together to form the portion 23. The portion 23 is then bent back toward the tooth to lie flat against it, so that it does not irritate the portion of the cheek which lies opposite it and would otherwise contact it. The pack 13 is then molded around and within the fixture 15, so that it extends over the site 14. The apparatus holds the pack securely in this way and it is not easily dislodged. This particular manner of holding the surgical pack 13 is particularly adaptable in the case of the free gingival graft, wherein the site 14 is a "donor" site. The invention, therefore, serves the purpose of retaining a periodontal or surgical pack or dressing in the oral cavity subsequent to various types of surgery, especially periodontal surgery. The fixture is anchored firmly to the tooth. The surgical pack material is molded around and within the fixture and against the surface of the tooth to which it is anchored and against adjacent teeth. The pack covers the surgical site and is then allowed to set. This is especially useful at the donor site of a gingival graft which would be on the palate where it is extremely difficult to maintain a pack. The well-retained pack gives post-operative comfort to the patient, protects the tissue from trauma and irritation, and prevents hemorrhage during early healing.

In addition to use in surgical situations, the ease with which this retention system can be installed and the high holding reliability make it practical for retaining medication in desired locations in the mouth. For example, the system has been found effective in retaining anti-bacterial agents in the periodontal pocket at the junction of tooth and gingiva for the required ten days. The system is easy to install and comfortable for the patient.

Figure 4:
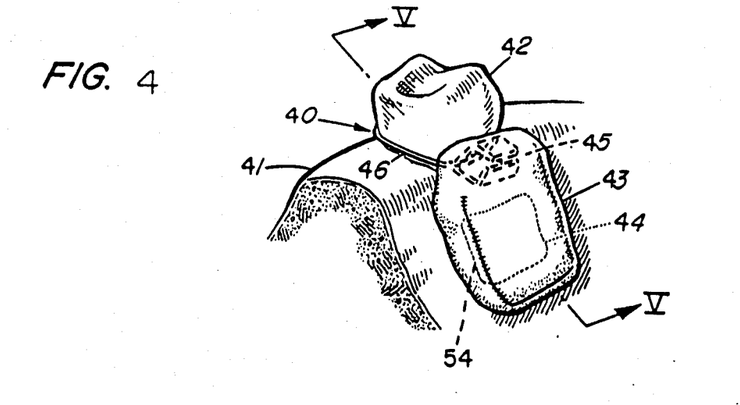
FIG. 4 is a perspective view of another oral pack retention device incorporating the principles of the present invention.

Referring now to FIG. 4, wherein are shown the general features of another embodiment of the invention, the oral pack retention system, indicated generally by the reference numeral 40, is shown in use in a patient's mouth, having a palatal tissue surface 41 and a tooth 42. The device is shown in use in holding a periodontal pack 43 over a surgical donor site 54 on the palate 41.

Figure 5:
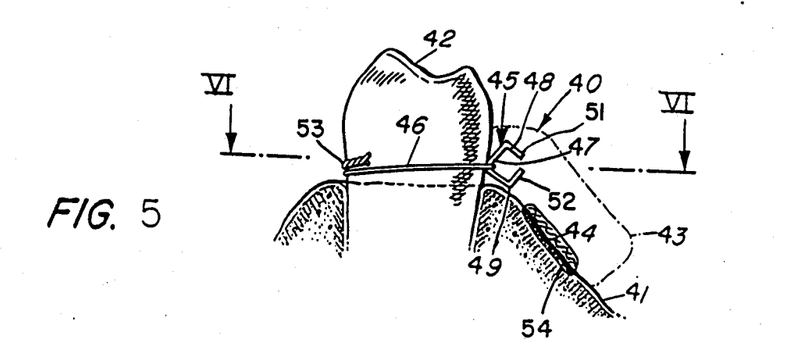
FIG. 5 is a vertical sectional view of the device show in FIG. 4 taken along the line V—V of FIG. 4.
Figure 6:
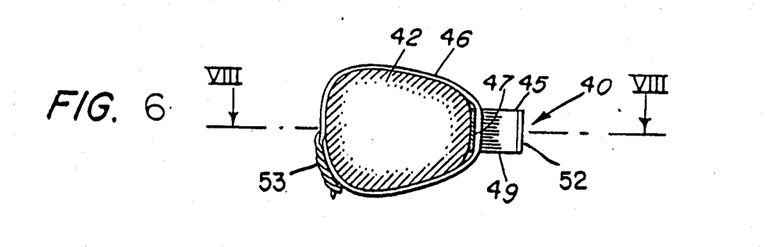
FIG. 6 is a plan view of the device as viewed on line VI—VI of FIG. 53.

FIGS. 5 and 6 show the details of the pack retention system 40 which has a retention device 45 located adjacent the tooth 42. The device is provided with a wire 46 which extends tightly around the tooth and is fastened to the fixture 45. As is evident in FIG. 5, the fixture 45 has an extruded shape, that is to say, it has a constant cross-section. The wire 46 and the fixture 45 are formed of a non-corrosive material such as stainless steel. The fixture 45 has a V-shaped central portion 47 the vertex of which faces the tooth. The fixture is fastened to the wire 46 by welding or the like along the interior of the vertex. The V-shape of the fixture 45 forms arms 48 and 49 which extend divergently away from the apex. The outer end of the upper arm 48 is provided with a downwardly-extending flange 51, while a similar flange 52 extends upwardly from the outer end of the lower arm 49. The flanges, therefore, extend toward one another to the extent that they each occupy approximately one-third of the space between the ends of the arms.

While this embodiment can be used to replace the first embodiment, this embodiment is particularly effective for using a rigid pack to hold a medicated dressing over a surgical wound. As described previously, standard surgical packs are formed of flexible polymers which can be placed in contact with the wound. There are various rigid polymers which are now used for temporary crowns and other applications not involving contact with sensitized tissue. When this rigid polymer is used as a pack, it takes advantage of the rigidity of the mounted fixture and allows substantial distance to exist between the nearest tooth and the wound. In order to allow the rigid polymer to be used, the wound and surrounding tissue are covered with a non-sticking surgical dressing 44 of the type known as Telfa pads. The rigid polymer is cured over the fixture and dressing to form a rigid pack. This rigid pack structure not only provides substantially better protection for the wound against food and tooth brushing, and substantially less irritation to the wound by the pack itself, but also, as stated above, allows the system to effectively protect wounds a significant distance from any tooth.

An additional benefit is that the pads can be filled with medication, which is then delivered to the wound under the pack. It is particularly effective to soak the pad in bovine thrombin, a coagulant that reduces bleeding in a fresh wound.

The V-shape of the fixture allows orientation and positioning of the fixture after the wire has been secured around the tooth. In many situations, the fixture can be set off from the tooth and gingiva. The rigidity of the wire holds the fixture in the desired orientation and position.

Figure 7:
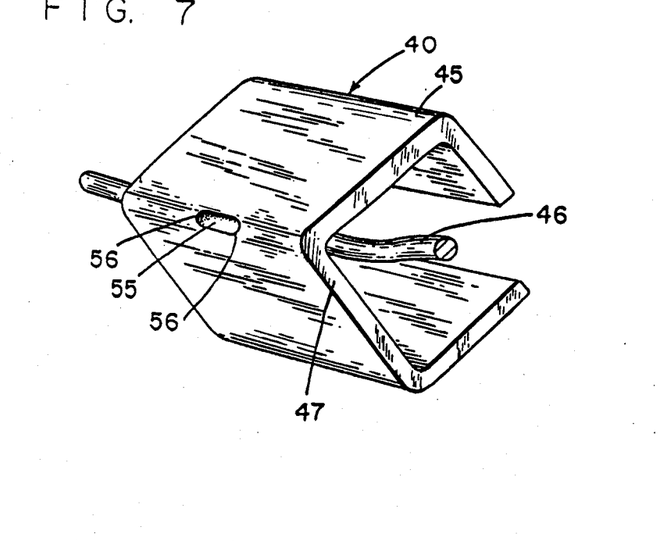
FIG. 7 is a detailed perspective view of the tooth-facing side of the device shown in FIG. 4.

In some situations, however, the shape of the tooth will cause the wire and fixture to tend to slide toward the gingiva. Contact between the fixture and gingiva should be avoided. To eliminate the sliding of the fixture, the tooth-facing side of the fixture is provided with a small scar 55, as shown in FIG. 7.

Figure 8:
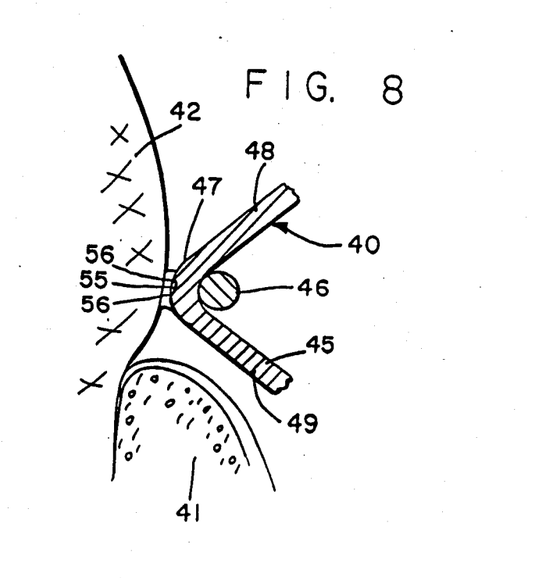
FIG. 8 is a detailed vertical sectional view of the device taken along line VIII—VIII of FIG. 6.

The scar is formed with sharp spines and edges 56. The spines and edges contact the tooth, as shown in FIG. 8, and reduce sliding problems. The scar can be effectively formed by placing the electric welding electrode at the point where the scar is desired when the wire and fixture are welded together.

Another application of this invention concerns the stabilization of teeth that have been reimplanted after traumatic loss or intentional removal during endodontics, that have become mobile, or that have been subject to orthodonic treatment. The invention is also suitable for stabilization of implants, especially of the "blade-vent" type. Standard stabilization techniques are difficult to apply and time consuming. Using the method of the present invention, a fixture is wired, in the manner described above, to each of the subject tooth and the teeth on each side. The uncured "rigid" pack material is applied to form a mass connecting all of the fixtures. The subject tooth is positioned and the pack material is allowed to cure to a rigid form. The resulting structure can remain in place until the tooth is stabilized. The structure can be removed far more easily than the structures resulting from prior techniques, and particularly with less chance of damaging the now stabilized tooth or implant.

Another aspect of this invention involves the use of the invention in the surgical and non-surgical treatment of periodontal disease at the interface between the tooth and the structures that contact and hold the tooth. It has been recognized for many decades that more teeth are lost in adults due to periodontal disease than due to dental caries. Since the advent of dental caries prevention, particularly involving the many ways of using fluoride, this shift in the causes of tooth loss has become even more exaggerated.

Instruments and methods have evolved for people to be able to remove plaque daily from all areas of the tooth; above, and in close proximity to the gingival attachment apparatus in people with healthy periodontal tissues or in those with relatively early disease with little destruction and minimal pocket formation. If pockets exists beyond this depth, then, it is impossible for the person to remove the plaque completely and the patient is no longer able to control or reverse the process. The disease is insidious and symptoms can be absent or easily ignored by patients. Of course, a well-trained, competent dentist can diagnose this disease at its earliest incipiencies (gingivitis).

In addition to many people having moderate or advanced periodontal disease, unfortunately, many more will join their ranks because, even when people are exposed to methods of effective plaque removal and its importance in preventing periodontal disease leading to loss of teeth, there is only a small rate of success in behavior modification. Similar low rates of success are experienced in other behavior modification endeavors.

It will be necessary to use therapeutic methods until better preventive methods are developed, or better behavior modification methods result in more widespread usage of existing time and energy consuming methods which require a high degree of motivation and self discipline.

Therapy has been, for the most part, scaling, root planing, and curretage, in the more moderate involvement, and surgery of various types for the more severely involved situations. There have been some research techniques demonstrated in this country and other countries involving a non-surgical technique using plastic strips or fibers to deliver antibiotics into periodontal pockets.

These techniques have demonstrated some efficacy, but can hardly be considered clinically acceptable and marketable. The periodontal dressing that holds the material containing the medication, is very frequently fractured and lost and the patient has to return for re-insertion of new medication bearing material and re-applying of the pack, possibly more than once. One of these techniques involves packing a small continuous fiber (containing tetracycline) around and around each tooth, having to pass the fiber in between the teeth each half a revolution. This is extremely tedious, time consuming, and is labor intensive. The patient is put through long appointments for small numbers of teeth.

If this technique was attempted to be used clinically, in private practice, the fee would have to reflect its frequent need to be redone, its labor intensiveness, and its excessive chair time.

Research has indicated that Minocycline (semi-synthetic tetracycline) is possibly more effective than tetracycline Systemic Minocycline lowered the amount of collagenase in periodontal pockets better than tetracycline.

It is also quite possible that Ibuprofen (an anti-inflammatory agent) might be very effective, delivered locally to periodontal pockets. Plastic strips containing Metronidazole have also been used with some success in reduction of depth of periodontal pockets. It may be found that other therapeutic agents may have a desired effect on a periodontal pocket.

It has been proven that a porous or permeable barrier between the tooth root and the soft tissue lining of the periodontal pocket, placed in close proximity to the periodontal ligament and in contact with the adjacent bone, encouraged coronal migration of ligamentary connective tissue cells on the uncovered root surface of the pocket, thereby reducing the depth of the pocket. Ordinarily, the barrier would be inserted after curretting of pocket granulation tissue from the soft tissue wall of the pocket. The barrier acted as a differential barrier in that it prevented gingival epithelium from growing down quickly and encouraged ligamentary connective tissue to migrate in the coronal direction and to form and insert principle fibers into cementum. The barrier also prevented connective tissue cells from bone and gingiva from populating the root surface. This is desirable, since, if the bone and/or gingival connective tissue cells are allowed to populate the root surface, less attachment and frequent root resorption occurs.

For the purposes of this specification, unless otherwise recited, it shall be assumed that teeth of the lower jaw are described. Therefore, terms such as "up" and "top" shall refer to the coronal direction.

It is an outstanding objective of this aspect of the present invention is to provide clinically acceptable methods of non-surgical therapy and modifications of surgical therapy, as well as materials and devices to stabilize and protect the components of the systems so that they remain intact, thereby extending their therapeutic effect for the entire time of recommended duration of therapy. Involved were a spectrum of armamenteria for flexibly treating the individual patient.

An objective of the invention would be to manufacture devices to be supplied to practitioners to insert between the tooth root and the gingiva, that is into the periodontal pocket in non-surgical cases, and to be placed between the root an the tissue that has been positioned against it after a surgical procedure. It is anticipated that a greater proportion of cases with greater periodontal destruction would be amenable to non-surgical therapy using this method.

The device would consist of a strip of material, with some flexibility, that would, in conjunction with others, adjacent to, or overlaping it, completely surround the tooth, to the depth of the pocket or bone, at the periodontal ligament. Although it would be possible to position the strip with its top at the gum line, it is preferred that the strip be provided with a tab which would extend at a slight angle from the pocket and which would serve as an area to be grasped with an instrument to facilitate insertion into the pocket. The tab would also serve to engage a pack that would be applied later. When the pack would be removed, automatic removal of most of the strips would occur because the tabs would be embedded in the pack.

The device, in addition to having some flexibility, would be a porous or permeable polymer, and therefore would be a barrier to tissue growth, but not to fluid. It would also be able to bear, and release medication at a controlled rate, over a long period of time.

It would to be formed at a temperature that would not cause the therapeutic to be decomposed.

Figure 9:
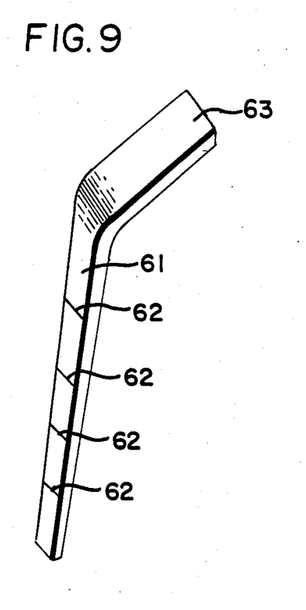
FIG. 9 is a perspective view of a strip adapted to be inserted into a periodontal pocket.

Each strip 61, as shown in FIG. 9, would be 3 to 5 mm wide and have indented lines 62 at 2 mm or 4 mm intervals or would be color-coded for different lengths. It might also have a tab 63. Pocket depth measurements would have been accomplished and recorded at examination.

The presence of medications in the pocket would reduce or eliminate infectious agents, reduce inflammation, and possible encourage some favorable migration of the periodontal attachment apparatus coronally. The barrier would also cause coronal migration at the attachment apparatus. In this sense, the barrier might be used without drug content. The pocket would have become shallower or non existent and free of infection and inflammation.

Figure 10:
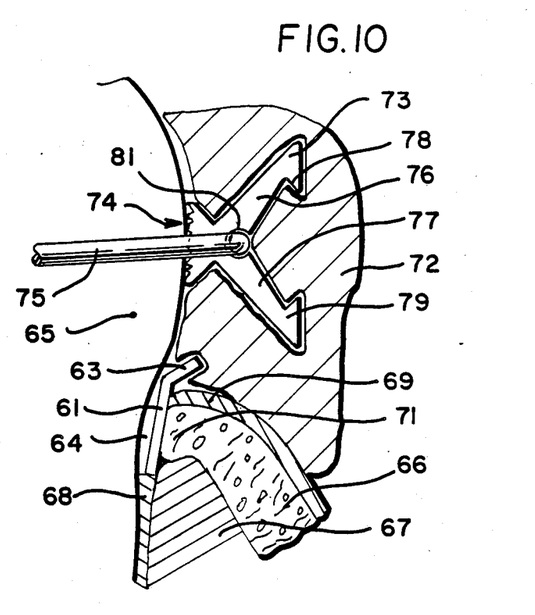
FIG. 10 is a sectional view of a strip of the type shown in FIG. 9, held in a periodontal pocket.
Figure 11:
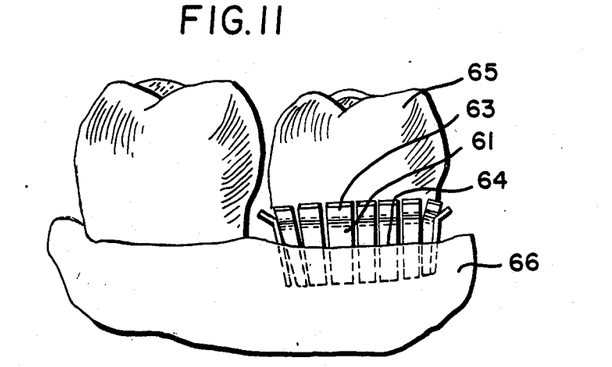
FIG. 11 is a perspective view of a number of strips of the type shown in FIG. 9, inserted into a periodontal pocket.

A typical non-surgical procedure using the present invention is shown in FIGS. 10 and 11. FIG. 11 shows the individual strips, including strip 61, inserted into the periodontal pocket 64, around tooth 65 and gum 66. The strips should be contiguous or should overlap to form, as nearly as possible, a continuos barrier around the tooth in the pocket.

FIG. 10 shows the arrangement of apparatus subsequent to the situation shown in FIG. 11. The strip 61 is positioned in the pocket 64, against the bone 67 and over the ligamentary connective tissue 68. On one side of the strip 61 is the tooth 65. On the other side of the strip 61 is the epithelium 69 and the gingival connective tissue 71. The differential barrier effect allows the ligamentary connective tissue to migrate up the tooth 65, but interferes with attachment of the epithelium 69 and gingival connective tissue 71 to the tooth. Once the strips are in place, a mass 72 of pack material is attached to the tooth 65 to hold the strips in place and to protect the pocket. The mass may be attached by direct adhesive action on the tooth, or by attachment to a retainer which is, in turn, attached to the tooth. The retainer 73 may be attached to the tooth by means of a strong adhesive such as zinc carboxylate cement, composite resin, or other adhesive, applied between the tooth and a broad textured foot 74. The retainer may also be attached by means of a cord or monofilament 75, tied around the tooth and retainer.

The preferred retainer is shown in FIG. 10. In particular is shown the constant cross-section, suitable for extrusion. The retainer would be formed of polymer. Extending from the foot and base would be two legs in Vee-shaped configuration. Each leg has an inwardly directly horn 78 and 79. At the base of the Vee-shape is a bore 81, which is open in an outward direction, the opening covering less than 180 degrees of the bore. This allows the monofilament to be snap-locked into the bore. FIG. 10 is not drawn to scale. Typically, the retainer would be approximately 3 mm in each direction, whereas the pockets and therefore the length of the strip less the tab would be 4 to 8 mm.

The pack material is then applied for attachment to the tooth and to the tab of the strip.

One level of periodontal disease that normally requires surgical treatment, is the presence of "bony defects", deep depressions in the bone underlying the tooth. The use of the medicated strips of the present invention, allows treatment of these bony defects in the surgical or nonsurgical context. After placement of the strips, freeze-dried bone or synthetic bone (hydroxy apatite), in a resorbable vehicle, is injected into the bony defect through a large-bore, bevel-point needle. Preferably, a leveraged syringe, such as a intraligamentary syringe, would be used. The needle would be pressed with sufficient force to pierce the periosteum over the bony defect outside the barrier, to place the bone matrix in the defect and thereby to aid the body in repair of the defect.

Another objective of this invention is to provide a spectrum of three different pack systems (one would be used with a retainer and two that would be adhesive and used without retainers) to be used with the above mentioned drug delivery and barrier system or with other techniques.

Another objective of the invention is to provide a new design and different materials for a pack retainer. The retainer, shown in FIG. 10, is constructed of a polymer with a slight degree of flexibility. It would probably be radio-opaque. The filament (flexible mono filament similar to nylon mon filament suture material) snap fits into retainer in area designed to receive it, because the bore 81 has a slightly larger I.D. than O.D. of filament, and goes slightly more than on half the circumference.

One or two retainers can be used; labial, lingual or both. A series of three or four square knots are used to tighten the retainers to the tooth and secure them in place with the filament. Three or four square knots are necessary to prevent slippage as is usual with nylon mono filament sutures.

A conventional nonadhesive pack can be applied now that the retainer(s) is in place, or an improved nonadhesive pack can be used.

Another object of the invention is to provide a much stronger nonadhesive pack, to be used in conjunction with pack retainer, which is not as easily fracture as conventional pack, and is suitable for surgical and non-surgical techniques. The pack would be formed of a greatly improved zinc oxide powder and eugenol material such as the material described in U.S. Pat. No. 3,509,089 to Dougherty. The finely divided zinc oxide powder would be treated with hot vapors of propionic acid (0.5% to 3.0%) causing a surface layer of zinc propionate on the zinc oxide particles. This allows a large amount of higher molecular weight polymer to be incorporated into systems to provide greatly increased tensile and other strengths, without making it difficult to mix or apply.

Twenty parts by weight finely divided polymethyl methacrylate, are added to eight parts by weight, lead free zinc oxide, previously treated so that the zinc oxide particles have a coating layer of zinc propionate. Both powders are mixed with eugenol, and with 1.0% acetic acid as a catalyst. A powder-liquid ratio of 3:1 is used. In addition, minerals fillers and plasticisers can be added. Also fibers can be added; glass, polymer, etc.

Even greater strength can be achieved if the fibers selected were treated with organo-funtional silanes, or other agents which cause bonding of the fibers to the setting pack material, with the potential for some splinting action.

In place of hand mixing and applications there have been existing for some time, premeasured two compartment capsules for powder and liquid which can be activated (allowing liquid and powder contact) and mixed on a high speed automatic mixer. The capsule can become the container which allows a plunger from one end to express the contents through a syringe tip when a pin is removed from the syringe tip. Such an application system is sold by ESPE Premier Sales Corporation, Norristown, Pa. under the trademark "ESPE KETAC-FIL capsulated system".

A modification of the above would be to use a capsule that would thread onto or into an adaptor for an intraligamentary syringe, such as that sold by Kinetic Instruments Inc., Bethel, Conn., under the trademark "MILTEX Intralig.".

Another objective of the invention is to provide an even stronger, adhesive to tooth structure (retainerless) pack. It would be strong enough to provide some temporary splinting action, for teeth with mobility.

The material would be an anhydrous zinc polycarboxylate cement (a polyelectrolyte cement) which would be mixed with distilled water. This also can be hand mixed and applied or utilize one of the methods above.

Small areas of tooth structure are prepared by cleansing with flour of pumice and water, or non-fluoride, non-oily, prophylaxis paste. These adhesion areas (cross-hatched) are designated as numeral 94 in FIG. 12. The pack is very strong and very adhesive. All tooth surface where pack will be except small areas for desired adhesion, would be coated with a thin film of separating medium, probably mineral oil. These nonadhesion areas (hatched) are designated as numeral 95 in FIG. 12. The areas of adhesion should be recorded for easier removal.

It may be possible to eliminate the need for the separating medium on teeth when using zinc polycarboxylate adhesive pack, in conjunction with the strips in the pockets. This technique would involve use of strips which are tabless, but which are long enough to extend out of the pocket and along the tooth surface almost to the highest point to which the adhesive back would be applied. The pack would therefore primarily contact areas of the strip and, at those points, there would be no adhesion to the tooth. The pack would extend above the top of the strip, slightly, to create very limited areas of adhesion. These areas would create enough adhesion to allow the pack to stay in place as needed, but not so much adhesion that removing the pack would be difficult when removal was desired.

Figure 12:
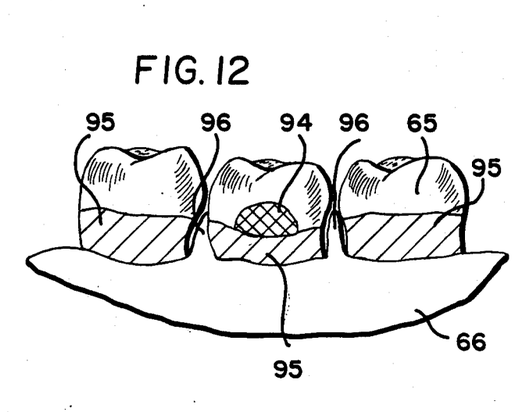
FIG. 12 is a perspective view showing prefered zones of adhesion and release on teeth.
Figure 13:
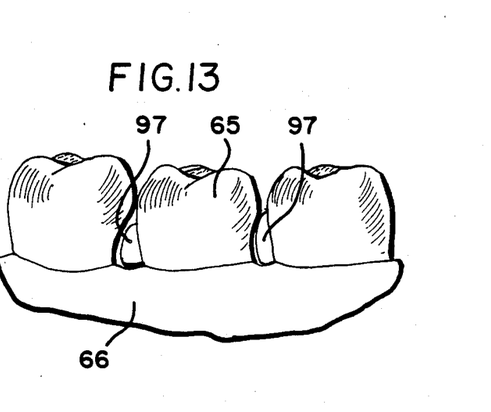
FIG. 13 is a perspective view of teeth showing interdental release blocks.

If there has not been destruction of the interdental papillae 96, which papillae are present in FIG. 12 and absent in FIG. 13, then the pack can not be allowed to attach to the pack on the other side of the teeth.

If the interdental papillae have been destroyed to any more than a very small amount, then a blocking agent 97 should be used, or it would be very difficult to remove if there was connection of this very strong material from one side of the teeth to the other. The blocking agent would be formed of a release material, preferably a temporary filling material or sealing material such as those materials sold under the trademarks "CAVIT"(Premier) or "SUNFILL" (Kenetic). As shown in FIG. 13, the blocking agent 97 would be placed in the interdental spaces. It would keep the pack from between the teeth, would ease removal of the pack, and is itself easily removed.

Another object of the invention would be to provide yet another pack that would be adhesive, (retainerless) strong enough for splinting action of mobile teeth, and more cosmetic.

This would be a light-curved composite resin. Small areas would be cleansed, but they would also be etched, and no separating medium would be necessary, but a bonding agent would be applied. The areas of adhesion should be recorded or be of two different colors for easier removal. Because the resin is so strong, it can be used in very thin layers and still function as a pack. For that reason, it can be light-cured very quickly.

The material would be supplied in a syringe or be adaptable to an intraligamentary syringe. A blocking agent would be needed if interdental papillae are not intact, as described with other pack. After it has been applied, it can be sculpted with an instrument, dipped in bonding agent to prevent material from sticking to instrument. The pack would then be light-curved. A longer and narrower light-curving tip could be designed; used for greater efficiency. The material could even be polished for optimum cosmetics.

Another object of the invention is to improve the tensile strength of composite resins. Other properties may also be improved in the process of doing this. The resin mass would include microfibers, pretreated with agents, to cause them to be bonded to the setting resin in contact with the the resin and to the other components of the composite. The microfibers would probably be treated with organo-functional silanes.

These products would probably not only be strong enough for use as posterior restorative materials, but could also be used for pontics and crowns; cured in the mouth or as a dental laboratory procedure.

It may be necessary for a layer of microfil composite to be added to the surface for better smoothness and polishability. This could be accomplished with templates for controlling thickness of microfil layer as well as templates for controlling size and shape of pontics and crowns.

Some of the composite formulations described in the specification are improvements of existing formulations used in dentistry for other purposes. These other purposes do not require the high tensile strength required for the present use.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. An oral pack retention system for use in covering a location in the mouth which is adjacent a tooth, comprising:
   (a) medication delivery means adapted to be placed at said location for delivering medication to the location,
   (b) a mass of pack material adapted to be placed against said medication delivery means and said tooth for retaining the medication delivery means in position with respect to the location, and
   (c) connecting means for connecting said mass of pack material to said tooth so that said mass of pack material remains in said medication delivery means retaining position.

2. An oral pack retention system as recited in claim 1, wherein the medication delivery means is a thin strip, the location is a peridontal pocket, and the strip is placed in the pocket.

3. An oral pack retention system as recited in claim 1, wherein the medication delivery means forms a differential barrier which encourages desired repair and discosurages undesired repair.

4. An oral pack retention system as recited in claim 1, wherein the medication delivery means delivers the medication at a controlled rate.

5. An oral pack retention system as recited in claim 1, wherein the connecting means comprises a connector of constant cross-section.

6. An oral pack retention system as recited in claim 1, wherein the connecting means comprises a separate connector which is attached to said tooth with adhesive.

7. An oral pack retention system as recited in claim 1, wherein said mass of pack material is adhesively bonded to said tooth.

8. An oral pack retention system as recited in claim 7, wherein a portion of the tooth is coated with a release agent to prevent adhesion of said mass of pack material on that portion.

9. An oral pack retention system as recited in claim 1, wherein a blocking mass is positioned in an interdental space to prevent contact between a mass of said pack material which is placed on one side of the tooth and a mass of said pack material which is placed on the other side of the tooth.

10. An oral pack retention system as recited in claim 1, wherein said mass of pack material is formed of a composite of formable material and fiberous material.

11. An oral pack retention system as recited in claim 1, wherein the mass includes microfibers treated to increase their adhesion with the rest of the mass and to thereby increase the tensile strength of the mass.

* * * * *